United States Patent
Le Garrec et al.

(10) Patent No.: US 6,780,324 B2
(45) Date of Patent: Aug. 24, 2004

(54) PREPARATION OF STERILE STABILIZED NANODISPERSIONS

(75) Inventors: Dorothée Le Garrec, Montréal (CA); Meriam Kabbaj, Montréal (CA); Jean-Christophe Leroux, Montréal (CA)

(73) Assignee: Labopharm, Inc., Quebec (CA)

( * ) Notice: Subject to any disclaimer, the term of this patent is extended or adjusted under 35 U.S.C. 154(b) by 193 days.

(21) Appl. No.: 10/101,572

(22) Filed: Mar. 18, 2002

(65) Prior Publication Data

US 2003/0175313 A1 Sep. 18, 2003

(51) Int. Cl.[7] ............................................. B01D 11/00
(52) U.S. Cl. ........................ 210/639; 210/649; 264/5; 424/489
(58) Field of Search .................... 210/634, 639, 210/644, 649, 702, 708, 709, 729, 774, 806; 424/450, 451, 455, 489, 490; 264/5, 8, 9

(56) References Cited

U.S. PATENT DOCUMENTS

| | | | |
|---|---|---|---|
| 4,311,712 A | 1/1982 | Evans et al. | |
| 4,370,349 A | 1/1983 | Evans et al. | |
| 4,745,160 A | 5/1988 | Churchill et al. | |
| 4,997,454 A | * | 3/1991 | Violante et al. .......... 23/305 A |
| 5,019,400 A | * | 5/1991 | Gombotz et al. .......... 424/497 |
| 5,543,158 A | 8/1996 | Gref et al. | |
| 6,322,805 B1 | 11/2001 | Kim et al. | |

FOREIGN PATENT DOCUMENTS

| EP | 0 397 307 A2 | 11/1990 |
| EP | 0 520 888 A1 | 12/1992 |
| EP | 0 583 955 A2 | 2/1994 |

OTHER PUBLICATIONS

PGPUBS Document US2003/0202978, filed on Oct. 30, 2003, Maa et al.*

\* cited by examiner

*Primary Examiner*—Joseph Drodge
(74) *Attorney, Agent, or Firm*—McHale & Slavin, P.A.

(57) ABSTRACT

The instant invention is directed toward a process for the production of a sterile, stabilized nanodispersion or loaded micelle comprising a polymer and a biologically active composition; particularly to nanodispersions produced by rehydration of a freeze-dried cake produced via the direct lyophilization of a stabilized solution comprising a polymer, such as an amphiphilic block copolymer or a small molecular weight surfactant, a biologically active agent, an optional additive, and a suitable solvent.

15 Claims, 2 Drawing Sheets

PREPARATION OF STERILE STABILIZED NANODISPERSIONS

FIELD OF THE INVENTION

This application relates to sterile, stabilized nanodispersions or micelles comprising a polymer and a biologically active composition; particularly to nanodispersions or micelles produced by rehydration of a freeze-dried cake produced via the direct lyophilization of a solution comprising a dispersing agent such as an amphiphilic block copolymer, or a small molecular weight surfactant, a biologically active composition, a suitable solvent, and optionally, an additive.

BACKGROUND OF THE INVENTION

Many important biologically active agents, such as drugs, are hydrophobic and have limited solubilities in water. In order to attain the expected therapeutic effect of such agents, it is usually required that a solubilized form or nanodispersed form of the agent be administered to a patient.

Thus, a number of methods have been developed which are based on the use of auxiliary solvents; surfactants; soluble forms of the drug, e.g., salts and solvates; chemically modified forms of the drug, e.g., prodrugs; soluble polymer-drug complexes; special drug carriers such as liposomes; and others. Indeed, the use of amphiphilic block copolymer micelles has attracted a great deal of interest as a potentially effective drug carrier which is capable of solubilizing a hydrophobic drug in an aqueous environment.

Each of the above methods is hampered by one or more particular problems, e.g., the method based on the use of surfactant micelles to solubilize hydrophobic drugs has problems in that some of the surfactants are relatively toxic and that precipitation of hydrophobic drugs occurs when subjected to dilution.

A variety of methods and procedures have been described in the prior art for preparing nanodispersions of hydrophobic compounds, particularly pharmaceutical preparations. It is known to incorporate hydrophobic biologically active agents having limited solubility in an aqueous or hydrophilic environment into block copolymers which form micelles capable of acting as carriers for the biologically active agents.

A variety of methods have been utilized, either alone or in combination, in order to incorporate or solubilize one or more biologically active agents, within polymer carriers. Included among these prior art methods are:

(1) Stirring

This method consists in adding the drug to a polymeric micelle solution and permitting the drug to dissolve in the micellar core. Such a procedure yields generally poor entrapment efficiency mainly because of the poor affinity of the drug for the aqueous medium. The water solution can then be freeze dried;

(2) Heating

A drug and a block copolymer are dissolved in an organic solvent and the solvent is evaporated off at an elevated temperature (from about 40° C. to about 80° C. under a nitrogen atmosphere or by rotary evaporator under vacuum). The resulting mixture is kept at a temperature of 20° C. to about 80° C., preferably at about 40–70° C., for 2 hours. Then, warm water (about 40° C. to about 70° C.) is added thereto, and the mixture is stirred until a polymeric micelle containing drug is formed.

(3) Ultrasonic Treatment

A mixture of a drug and an aqueous solution of a block copolymer is subjected to ultrasonic treatment for a period ranging from about 1 second to 1 hour and then stirred at room temperature to obtain micelles containing the drug.

(4) Solvent Evaporation

A drug is dissolved in a water-immiscible organic solvent, for example, dichloromethane, chloroform and the like, and then added to an aqueous solution of a block copolymer. Subsequently, the organic solvent is slowly evaporated off, e.g. at 25–40° C. while stirring, optionally under vacuum, and then filtered to remove undissolved drug.

(5) Dialysis

A drug and a block copolymer are dissolved in a water-miscible organic solvent. The solution is dialyzed against a buffer solution and then against water.

In the dialysis method, suitable water-miscible organic solvents for dissolving drugs may include members selected from the group comprising acetonitrile, dimethylformamide (DMF), dimethylsulfoxide (DMSO), dioxane, dimethylacetamide (DMAC) and the like.

The unloaded drug can diffuse with the organic solvent and/or precipitate in the dialysis bag. The precipitated drug can be removed by filtration. The colloidal dispersion is then generally freeze-dried.

(6) Emulsification-Evaporation/Salting Out Procedure

The drug and polymer are dissolved in a water-immiscible organic solvent which is emulsified in water. The aqueous phase may or may not contain stabilizers. The organic solvent is then removed by evaporation or other methods. If needed, the nanodispersion can be further purified to remove the stabilizers. Then, the colloidal dispersion can be freeze-dried.

(7) Spray-Drying

The drug is dissolved in an organic solvent which is then nebulized so as to obtain drug loaded nanoparticles. Such a process may not be adapted for temperature-sensitive drugs and is not optimal to produce particles of less than 1 μm.

(8) Micronization/Controlled Precipitation/High Pressure Homogenization

These methods are aimed at producing nanoscaled drug dispersions. Such techniques can be applied to almost any kinds of hydrophobic drugs. All require specific specialized equipment and/or are difficult to control.

Each of the above procedures are associated with certain drawbacks. For example, with some of the procedures the stabilizers need to be removed. Others yield poor entrapment efficiencies (e.g. equilibration), relatively large particle sizes (e.g. spray drying) or are time-consuming (e.g. dialysis).

DESCRIPTION OF THE PRIOR ART

Many studies, literature articles and patents have been directed toward the use of amphiphilic block copolymers having surfactant-like properties, particularly regarding their use as carriers for hydrophobic drugs.

For example, EP No. 0397307A2 discloses polymeric micelles of an AB type amphiphilic diblock copolymer which contains poly(ethylene oxide) as the hydrophilic component and poly(amino acid derivatives) as the hydrophobic component, wherein therapeutically active agents are chemically bonded to the hydrophobic component of the polymer.

EP No. 0583955A2, on the other hand, discloses a method for physically incorporating hydrophobic drugs into amphiphilic diblock copolymer micelles described in EP No. 0397307A2. This method, thus, solves the above disadvantage of the chemical bond type polymeric micelle drug U.S. Pat. No. 4,745,160 discloses a pharmaceutically or veterinary acceptable amphiphilic, non-cross linked linear, branched or graft block copolymer having polyethylene glycol as the hydrophilic component and poly(D-, L- and DL-lactic acids) as the hydrophobic components. In the preparation process, a water-miscible and lyophilizable organic solvent is used. When a mixture of the polymer, drug and organic solvent is mixed with water, precipitates are formed and then the mixture is directly lyophilized to form particles. Thereafter, when this particle is dispersed in water, it forms a colloidal suspension containing fine particles wherein hydrophilic components and hydrophobic components are mixed.

In contrast to that which is disclosed in the prior art, the present invention forms a clear solution that can be sterilized by filtration (220 nm pore size filter) prior to freeze-drying, and yields a storable powder which is readily reconstituted. What is particularly unique, is that the micelle or nanodispersion is produced directly and spontaneously upon addition of an aqueous medium. This is in direct contrast to prior art processes which must first produce a nanodispersion which is subsequently lyophilized and then reconstituted. Furthermore, the instant process suffers no loss of drug during the loading procedure.

U.S. Pat. No. 6,322,805 discloses a biodegradable polymeric drug carrier micelle composition capable of solubilizing a hydrophobic drug in a hydrophilic environment. The patent discloses a biodegradable polymeric drug carrier micelle and a hydrophobic drug wherein the drug is physically trapped within and not covalently bonded to the polymeric drug carrier micelle. The drug carrying micelle is capable of dissolving in water to form a solution thereof, and the drug carrier comprises an amphiphilic block copolymer having a hydrophilic poly(alkylene oxide) component, and a biodegradable hydrophobic polymer component selected from the group consisting of poly(lactic acid), poly(glycolic acid), poly(lactic-co-glycolic acid), poly($\epsilon$-caprolactone), a derivative thereof and a mixture thereof. The disclosed micelle is characterized as a solubilizing agent for a hydrophobic drug. The drug solution thus obtained may be freeze-dried for long-term storage, and the lyophilized biodegradable polymeric micelle-type drug composition may be restored to its original solution by using water or an isotonic solution. This patent also fails to disclose or suggest a process wherein a sterile nanodispersion is spontaneously created upon reconstitution of a lyophilized cake.

U.S. Pat. No. 5,543,158 discloses nanoparticles or microparticles formed of a block copolymer consisting essentially of poly(alkylene glycol) and a biodegradable polymer, poly(lactic acid). In the nanoparticle or microparticle, the biodegradable moieties of the copolymer are in the core of the nanoparticle or microparticle and the poly(alkylene glycol) moieties are on the surface of the nanoparticle or microparticle in an amount effective to decrease uptake of the nanoparticle or microparticle by the reticuloendothelial system. In this patent, the molecular weight of the block copolymer is too high to be soluble in water, and a nanoparticle can only be prepared by first dissolving the block copolymer and a drug in an organic solvent, forming an o/w emulsion by sonication or stirring, and then collecting the precipitated nanoparticles containing the drug. The patent fails to provide the concept of solubilization of hydrophobic drugs, nor does it teach or suggest the formation of a clear, sterilizable solution containing the polymer/drug blend and subsequent lyophilization thereof, resulting in a readily dispersible nanodispersion, formed upon reconstitution.

EP 0520888 A1 discloses a nanoparticle made of a poly(lactic acid) and poly(alkylene oxide) block copolymer. A high molecular weight poly(lactic acid) is used and a surfactant is employed in preparing a colloidal suspension of the nanoparticles. In this patent, nanoparticles are prepared by dissolving the block copolymer and a drug in an organic solvent, emulsifying the organic solution in water, and evaporating the organic solvent to precipitate the nanoparticles containing the drug. The resulting nanoparticles are fine particles having both hydrophilic and hydrophobic components and they are not soluble in water.

U.S. Pat. Nos. 4,370,349 and 4,311,712 disclose a process for preparing a freeze-dried, potential liposome, mixture which comprises either (a) dissolving at least one liposome-forming amphiphilic lipid, at least one biologically-active compound, and optionally one or more adjuvants, in a suitable solvent, and then freeze-drying the solution, or (b) preparing by any known method an aqueous liposome composition containing at least one biologically-active compound, and then freeze-drying the said aqueous liposome composition. The patents are particularly directed toward a process for preparing an aqueous liposome composition which comprises dispersing said freeze-dried, potential liposome, mixture, obtained by procedure (a) or (b), in a suitable aqueous medium. The process of the instant invention is not directed toward liposome production.

The patents fail to disclose the formation of a clear solution that can be sterilized by filtration (e.g. by use of a filter media having a pore size of about 220 nm) prior to freeze-drying, yields a storable powder which is readily reconstituted, and suffers no loss of drug during the loading procedure. Furthermore, the patents fail to teach a method for producing a sterile drug formulation which, upon the addition of water, produces drug-loaded micelles or drug nanodispersions stabilized by an amphiphilic biodegradable polymer.

SUMMARY OF THE INVENTION

In order to overcome the problems encountered by the prior art, the instantly disclosed invention relies on the lyophilization of an organic solvent or mixture thereof, or a mixture of water and organic solvent in which the biologically active agent, e.g. a drug, the dispersing agent, e.g. a polymer, copolymer, small molecular weight surfactant, or the like, and optionally an additive, non-limiting examples of which include a bulk forming additive, a cryoprotectant, and a lyoprotectant, is dissolved. Such a solution can be sterilized by filtration before lyophilization and subsequently freeze-dried, forming a powder or cake. The resulting freeze-dried material can be stored and then redispersed prior to use by the addition of an aqueous solution. The organic solvent can be collected on the condenser and recycled for future use.

The instant process illustrates a simple and elegant procedure for directly obtaining nanodispersions upon reconstitution, thereby resulting in the formation of drug-loaded micelles or drug nanodispersions which are stabilized by a suitable dispersing agent, e.g. an amphiphilic biodegradable polymer or copolymer, or alternatively a small molecular weight surfactant. There is no loss of the drug during the loading procedure.

Examples of suitable dispersing agents include, but are not limited to amphiphilic polymers such as linear, branched or star-shaped block amphiphilic copolymers where the hydrophilic part may include at least one member selected from a group consisting of poly(ethylene oxide), poly(N-vinylpyrrolidone), poly(N-2-hydroxypropylmethacrylamide), poly(2-ethyl-2-oxazoline), poly(glycidol), poly(2-hydroxyethylmethacrylate), poly (vinylalcohol), polymethacrylic acid derivatives, poly (vinylpyridinium), poly((ammoniumalkyl)methacrylate), poly((aminoalkyl)methacrylate) and combinations and derivatives thereof;

and wherein the hydrophobic segment may include at least one member which is selected from a group consisting of a poly(ester), poly(ortho ester), poly(amide), poly(ester-amide), poly(anhydride), poly(propylene oxide), poly (tetrahydrofuran) and combinations thereof.

The poly(ester) may be at least one member selected from a group consisting of poly(ε-caprolactone), poly(lactide), poly(glycolide), poly(lactide-co-glycolide), poly(hydroxy alkanoates) (e.g. poly (γ-hydroxybutyrate), poly(δ-hydroxy valerate)), poly (β-malic acid), and derivatives thereof. Non-limiting illustrative examples of low molecular weight surfactants may include at least one member selected from the group consisting of sodium lauryl sulfate, hexadecyl pyridinium chloride, polysorbates, sorbitans, poly(oxy ethylene) alkyl ethers, poly(oxyethylene) alkyl esters and the like, including various combinations thereof.

Without limiting the scope of the present invention, suitable biologically active agents for incorporation in a nanodispersion produced in accordance with the teachings of the instant invention may include agents such as anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, and circulatory disease rem-edies. In their broadest sense, the "biologically active agents" of the present invention will include both human and veterinary medicaments, hormones, marker compounds, and the like.

The instant invention is most suitable for the manufacture of formulations containing biologically active agents which are sensitive or which may be degraded by exposure to adverse pH, temperature, and certain types of solvent envi-ronments.

Hydrophobic drugs which are of particular interest for incorporation in the present invention may include, but are not limited to members selected from the group comprising paclitaxel, doxorubicin, melphalan, docetaxel, teniposide, etoposide, daunomycin, vinblastine, indomethacin, ibuprofen, cyclosporine, tacrolimus, ketoconazole, ampho-tericin B, fenobibrate and biphenyl dimethyl dicarboxylate (DDB).

Suitable solvents or mixtures thereof will have the ability to dissolve appropriate amounts of the drug, without dena-turation or degradation thereof. Preferred solvents (or mix-tures of solvents) should remain solid during the freeze-drying process and should be relatively inert with regard to rubber seals. The solvent should also be easily removed under reduced pressure. While numerous solvents are capable of functioning in accordance with the process of the instant invention, non-limiting illustrative examples of such solvents include t-butanol, n-butanol, dioxane, pyridine, pyrimidine, and piperidine ,which are useful either alone or in combination, and may be further admixed, e.g. with water, to form a binary mixture. It is known that the latter 4 solvents may pose potential toxicity problems.

Other solvents may be added in small amounts (<10%) to facilitate the dissolution of the drug.

Accordingly, it is a principle objective of the instant invention to provide a process for the formation of a sterile, loaded micelle or nanodispersion comprising an amphiphilic biodegradable polymer.

It is a further objective of the instant invention to provide a process whereby a clear solution of the biologically active agent, polymer and optionally an additive (e.g. a bulk forming agent, a cryoprotectant, a lyoprotectant) and/or stabilizer is initially formed with a suitable solvent prior to lyophilization.

It is a further objective of the instant invention to provide a process whereby the solvent used in forming the clear solution is recyclable.

It is a still further objective of the invention to produce a stable freeze-dried cake which is readily dispersible to form a stabilized drug nanodispersion.

Other objectives and advantages of this invention will become apparent from the following description taken in conjunction with the accompanying drawings wherein are set forth, by way of illustration and example, certain embodiments of this invention. The drawings constitute a part of this specification and include exemplary embodi-ments of the present invention and illustrate various objec-tives and features thereof.

DETAILED DESCRIPTION OF THE INVENTION

Figure 1:
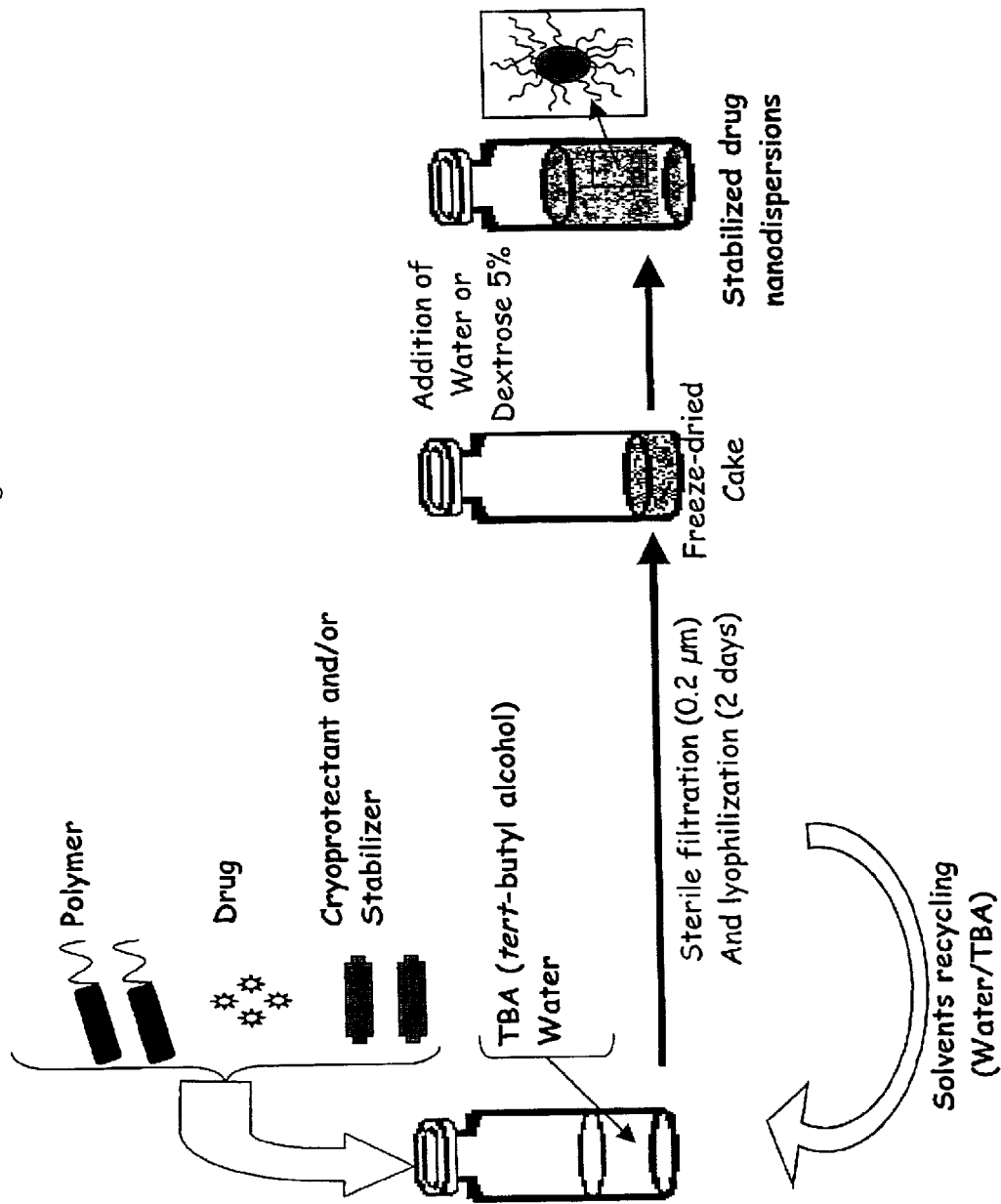
FIG. 1 is a schematic representation of the drug loading procedure using tert-butyl alcohol.

In accordance with the schematic representation set forth in FIG. 1, predetermined amounts of biologically active agent, dispersing agent, e.g. a suitable polymer, copolymer or small molecular weight surfactant and, optionally, an additive, e.g. a cryoprotectant/ a lyoprotectant/ a bulk form-ing agent or the like (e.g. commercially available poly (vinylpyrrolidone) Kollidon 12 PF® or 17 PF®, BASF) and/or additional stabilizers are dissolved in a suitable solvent, e.g. tert-butyl alcohol (TBA) or a binary mixture of TBA and water. For purposes of this invention cryoprotectant, lyoprotectant and bulk forming agents will be used interchangeably and referred to as an "additive". Other suitable additives include, but are not limited to poly(ethylene glycol), sugars (lactose, trehalose), polyols (mannitol) and amino acids soluble in the solvent or solvent mixture. As broadly recited herein, the term "solvent" is understood to mean a single solvent, a mixture of solvents, or a binary mixture of one or more solvents and water. In one illustrative embodiment, additional dissolution enhancing means may be employed to aid in the forming of a solution. Illustrative, but non-limiting examples of said dissolution enhancing means may include a process, for example, wherein the mixture may be vortexed and sonicated for 30 sec, if needed. For some polymers, the solution may also need to be heated to speed up dissolution. The clear solution thus obtained is stirred gently on a rotary shaker table at room temperature for 30 minutes. The solution is filtered, e.g. through a 0.2 μm filter. Subsequently, the solution is rapidly frozen and lyophilized for two days, whereby a dry cake of drug dispersed polymer is obtained.

Lastly, the freeze-dried cake may be rehydrated with a predetermined amount of water or a solution of saline 0.9% or dextrose 5%, whereby a stable nanodispersion is sponta-neously produced. The mean particle size is determined by dynamic light scattering.

TABLE 1

DRUG NANODISPERSIONS OBTAINED BY THE TERT-BUTANOL LYOPHILIZATION METHOD

| Ex | Polymer (w/w) | $M_n$* | Additive | Drug | Drug loading (w/w %)** | Drug concentration in water (mg/mL) | Mean size of resulting particles (water, 25° C.) (nm) |
|---|---|---|---|---|---|---|---|
| 1 | PVP-b-PDLLA (80:20) | 15079 | None | Paclitaxel | 15 | 0.75 | 66%: 210 ± 64<br>34% < 3 |
| 2 | PVP-b-PDLLA (80:20) | 15079 | Kollidon 12PF 50% (w/w) | Paclitaxel | 15 | 0.75 | 75%: 153 ± 66<br>25% < 3 |
| 3 | PVP-b-PDLLA (80:20) | 15079 | None | Indomethacin | 10 | 0.5 | 80%: 148 ± 41<br>20% < 3 |
| 4 | PVP-b-PDLLA (80:20) | 15079 | Kollidon 12PF 50% (w/w) | Indomethacin | 10 | 0.5 | 80%: 141 ± 42<br>20% < 3 |
| 5 | PHPMA-b-PCL-b-PHPMA (71:29) | 9100 | None | Paclitaxel | 15 | 0.75 | 64%: 270 ± 71<br>36%: 44 ± 15 |
| 6 | PHPMA-b-PCL-b-PHPMA (71:29) | 9100 | Kollidon 12PF 50% (w/w) | Paclitaxel | 15 | 0.75 | 60%: 177 ± 26<br>40% :33 ± 6 |
| 7 | PVP-b-PCL-b-PVP (79:21) | 11400 | None | Paclitaxel | 15 | 0.75 | 87%: 294 ± 57<br>12%: 60 ± 13<br>1%: 10 ± 2 |
| 8 | PHPMA-b-PCL b-PHPMA (79:21) | 13400 | None | Doxorubicin | 15 | 0.75 | 60%: 350 ± 65<br>40% < 3 |
| 9 | PHPMA-b-PCL-b-PHPMA (71:29) | 9100 | Kollidon 12PF 50% (w/w) | Paclitaxel | 5 | 0.75 | 65%: 32 ± 10<br>23%: 255 ± 75 |

**Based on the amount of (polymer + drug)
Nomenclature of the polymers:
PVP-b-PDLLA: Poly(N-vinyl-2-pyrrolidone)-block-poly(D,L-lactide)
PHPMA-b-PCL-b-PHPMA: poly(N-2-hydroxypropyl methacrylamide)-block-poly(ε-caprolactone)-block-poly(N-2-hydroxypropyl methacrylamide)
PVP-b-PCL-b-PVP: poly(N-vinyl pyrrolidone)-block-poly(ε-caprolactone)-block-poly(N-vinyl pyrrolidone)

Table 1 shows that upon the addition of water, colloidal drug dispersions (<1 μm) were spontaneously obtained.

Figure 2:
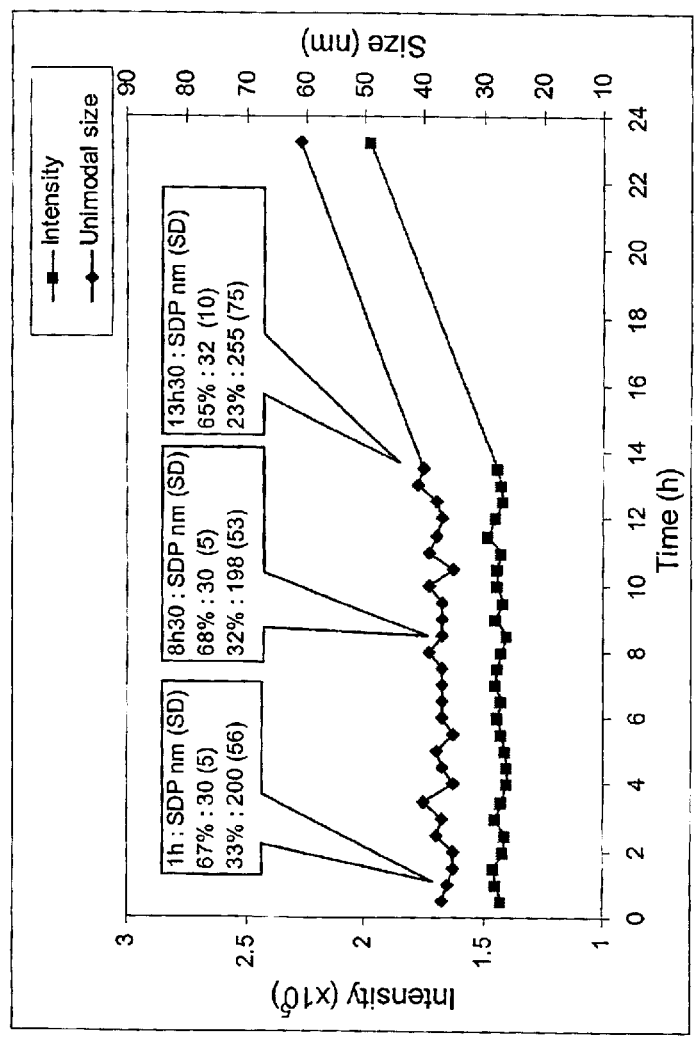
FIG. 2 shows the stability of formulation 9 over time following the addition of water.

FIG. 2 shows the stability of formulation 9 following the addition of water. The obtained solution was optically transparent suggesting the formation of polymeric micelles (or secondary aggregates of polymeric micelles). This formulation was stable for at least 13 hours when kept at room temperature.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures. One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for the production of a loaded micelle containing a biologically active agent comprising:
    forming a solution including at least one dispersing agent, at least one biologically active agent, and at least one solvent;
    lyophilizing said solution wherein a solid product is formed; and
    rehydrating said solid product;
    whereby said loaded micelle is produced.

2. The product produced in accordance with the process of claim 1.

3. A process for the production of a loaded micelle containing a biologically active agent comprising:
    forming a solution including at least one dispersing agent, at least one biologically active agent, at least one additive, and at least one solvent;
    lyophilizing said solution wherein a solid product is formed; and
    rehydrating said solid product;
    whereby said loaded micelle is produced.

4. The product produced in accordance with the process of claim 3.

5. A process for the production of a stabilized nanodispersion or loaded micelle containing a biologically active agent comprising:
    forming a solution including at least one dispersing agent, at least one biologically active agent, and at least one solvent;
    filtering said solution to yield a sterile filtrate;

lyophilizing said filtrate wherein a solid product is formed; and rehydrating said solid product;

whereby said stabilized nanodispersion or loaded micelle is produced.

6. The product produced in accordance with the process of claim 5.

7. A process for the production of a stabilized nanodispersion or loaded micelle containing a biologically active agent comprising:

forming a solution including at least one dispersing agent, at least one biologically active agent, at least one additive, and at least one solvent;

filtering said solution to yield a sterile filtrate;

lyophilizing said filtrate wherein a solid product is formed; and rehydrating said solid product;

whereby said stabilized nanodispersion or loaded micelle is produced.

8. The product produced in accordance with the process of claim 7.

9. A process in accordance with any one of claim 1 or 3 or 5 or 7 wherein said step of rehydrating includes combining said solid product with a sufficient amount of water, saline solution or dextrose solution.

10. A process in accordance with any one of claim 1 or 3 or 5 or 7 wherein said solvent is at least one solvent selected from the group consisting of t-butanol, n-butanol, dioxane, pyridine, pyrimidine, piperidine, combinations thereof, and binary mixtures including any of said solvents or combinations thereof in admixture with water.

11. A process in accordance with any one of claim 3 or 7 wherein said additive is at least one member selected from the group consisting of poly(vinylpyrrolidone), poly(ethylene glycol), lactose, trehalose, mannitol, amino acids soluble in said solvent, or combinations thereof.

12. A process in accordance with any one of claim 1 or 3 or 5 or 7 wherein said forming step further includes at least one dissolution enhancing means selected from the group consisting of sonicating, vortexing and heating.

13. A process in accordance with any one of claim 1 or 3 or 5 or 7 wherein said dispersing agent is at least one member selected from the group consisting of a polymer, a copolymer, a small molecular weight surfactant, and combinations thereof.

14. A process in accordance with any one of claim 1 or 3 or 5 or 7 wherein said biologically active agent is at least one member selected from the group consisting of anti-cancer drugs, antiphlogistic anodynes, immuno-suppressants, hepatism remedies, hormone compositions, chemotherapeutics, metabolic pharmaceuticals, digestive disease remedies, respiratory disease remedies, anti-allergic pharmaceuticals, central nervous system disease remedies, peripheral disease remedies, circulatory disease remedies, and combinations thereof.

15. A process in accordance with any one of claim 1 or 3 or 5 or 7 wherein said biologically active agent is at least one hydrophobic pharmaceutical composition selected from the group consisting of paclitaxel, doxorubicin, melphalan, docetaxel, teniposide, etoposide, daunomycin, vinblastine, indomethacin, ibuprofen, cyclosporine, tacrolimus, biphenyl dimethyl dicarboxylate, ketoconazole, amphotericin B, fenobibrate, and combinations thereof.

* * * * *